(12) United States Patent
Cox et al.

(10) Patent No.: US 7,242,474 B2
(45) Date of Patent: Jul. 10, 2007

(54) CYTOMETER HAVING FLUID CORE STREAM POSITION CONTROL

(76) Inventors: James A. Cox, 1842 - 26th Ave. NW., New Brighton, MN (US) 55112; Bernard S. Fritz, 1280 Deerwood Dr., Eagan, MN (US) 55123

( * ) Notice: Subject to any disclaimer, the term of this patent is extended or adjusted under 35 U.S.C. 154(b) by 373 days.

(21) Appl. No.: 10/899,607

(22) Filed: Jul. 27, 2004

(65) Prior Publication Data

US 2006/0023207 A1    Feb. 2, 2006

(51) Int. Cl.
    *G01N 21/00*    (2006.01)
(52) U.S. Cl. ........................ 356/338; 356/246
(58) Field of Classification Search ............... 356/244, 356/246, 335–343, 73, 440; 422/82.09; 436/63, 436/164, 172
    See application file for complete search history.

(56) References Cited

U.S. PATENT DOCUMENTS

| | | | |
|---|---|---|---|
| 3,661,460 A * | 5/1972 | Elking et al. ................ 356/36 |
| 3,822,095 A | 7/1974 | Hirschfeld |
| 3,976,862 A | 8/1976 | Curbelo |
| 4,352,558 A | 10/1982 | Eisert |
| 4,478,076 A | 10/1984 | Bohrer |
| 4,478,077 A | 10/1984 | Boher |
| 4,501,144 A | 2/1985 | Higashi et al. |
| 4,651,564 A | 3/1987 | Johnson et al. |
| 4,683,159 A | 7/1987 | Bohrer et al. |
| 4,695,034 A | 9/1987 | Shimizu et al. |
| 4,745,279 A | 5/1988 | Karkar et al. |
| 4,874,949 A | 10/1989 | Harris et al. |
| 4,911,616 A | 3/1990 | Laumann, Jr. |
| 4,983,038 A * | 1/1991 | Ohki et al. ................ 356/246 |
| 5,050,429 A | 9/1991 | Nishimoto et al. |
| 5,078,581 A | 1/1992 | Blum et al. |
| 5,082,242 A | 1/1992 | Bonne et al. |

(Continued)

FOREIGN PATENT DOCUMENTS

EP        1001326        5/1999

(Continued)

OTHER PUBLICATIONS http://www.micronics.net/tsensor.htm, pp. 1-4, downloaded Jun. 14, 2000.

(Continued)

*Primary Examiner*—Hoa Q. Pham
(74) *Attorney, Agent, or Firm*—Kris T. Fredrick (57) ABSTRACT

A cytometer having two or more chambers or regions in a containment structure of sheathing fluid that may be used to provide hydrodynamic focusing of another fluid having particles to be observed. The latter fluid may be a core stream which may have its lateral position in a flow or measurement channel affected by control of at least one of the parameters of the several segments of the sheathing fluid. The lateral position of the core stream may be aligned with a light source and detector for a count and observation of the particles. Electrical signals from the detector may be fed back to a processor which may control one or more parameters of the sheathing fluid in the various chambers or regions via pumps, valves, and flow and pressure sensors. This control of parameters may provide for the positioning of the core stream. This cytometer may be miniaturized.

14 Claims, 10 Drawing Sheets

U.S. PATENT DOCUMENTS

| | | | |
|---|---|---|---|
| 5,085,562 | A | 2/1992 | van Lintel |
| 5,096,388 | A | 3/1992 | Weinberg |
| 5,108,623 | A | 4/1992 | Cangelosi et al. |
| 5,129,794 | A | 7/1992 | Beatty |
| 5,171,132 | A | 12/1992 | Miyazaki et al. |
| 5,176,358 | A | 1/1993 | Bonne et al. |
| 5,185,641 | A | 2/1993 | Igushi et al. |
| 5,194,909 | A | 3/1993 | Tycko |
| 5,219,278 | A | 6/1993 | van Lintel |
| 5,224,843 | A | 7/1993 | van Lintel |
| 5,244,537 | A | 9/1993 | Ohnstein |
| 5,323,999 | A | 6/1994 | Bonne et al. |
| 5,441,597 | A | 8/1995 | Bonne et al. |
| 5,452,878 | A | 9/1995 | Gravesen et al. |
| 5,528,045 | A | 6/1996 | Hoffman et al. |
| 5,570,193 | A | 10/1996 | Landa et al. |
| 5,601,080 | A | 2/1997 | Oppenheimer |
| 5,616,501 | A | 4/1997 | Rodriguez |
| 5,633,724 | A | 5/1997 | King et al. |
| 5,683,159 | A | 11/1997 | Johnson |
| 5,716,852 | A | 2/1998 | Yager et al. |
| 5,726,751 | A | 3/1998 | Altendorf et al. |
| 5,757,476 | A | 5/1998 | Nakamoto et al. |
| 5,793,485 | A | 8/1998 | Gourley |
| 5,799,030 | A | 8/1998 | Brenner |
| 5,822,170 | A | 10/1998 | Cabuz et al. |
| 5,836,750 | A | 11/1998 | Cabuz |
| 5,863,502 | A | 1/1999 | Southgate et al. |
| 5,880,474 | A | 3/1999 | Norton et al. |
| 5,893,722 | A | 4/1999 | Hibbs-Brenner et al. |
| 5,901,939 | A | 5/1999 | Cabuz et al. |
| 5,922,210 | A | 7/1999 | Brody et al. |
| 5,932,100 | A | 8/1999 | Yager et al. |
| 5,948,684 | A | 9/1999 | Weigl et al. |
| 5,971,158 | A | 10/1999 | Yager et al. |
| 5,972,710 | A | 10/1999 | Weigl et al. |
| 5,974,867 | A | 11/1999 | Forster et al. |
| 6,007,775 | A | 12/1999 | Yager |
| 6,032,689 | A | 3/2000 | Tsai et al. |
| 6,082,185 | A | 7/2000 | Saaski |
| 6,097,485 | A | 8/2000 | Lievan |
| 6,106,245 | A | 8/2000 | Cabuz |
| 6,109,889 | A | 8/2000 | Zengerie et al. |
| 6,139,800 | A | 10/2000 | Chandler |
| 6,179,586 | B1 | 1/2001 | Herb et al. |
| 6,184,607 | B1 | 2/2001 | Cabuz et al. |
| 6,200,820 | B1 * | 3/2001 | Hansen et al. ............... 436/523 |
| 6,215,221 | B1 | 4/2001 | Cabuz et al. |
| 6,237,619 | B1 | 5/2001 | Maillefer et al. |
| 6,240,944 | B1 | 6/2001 | Ohnstein et al. |
| 6,249,341 | B1 | 6/2001 | Basiji et al. |
| 6,281,975 | B1 | 8/2001 | Munk |
| 6,382,228 | B1 | 5/2002 | Cabuz et al. |
| 6,473,172 | B1 | 10/2002 | Pelmulder |
| 6,549,275 | B1 | 4/2003 | Cabuz et al. |

FOREIGN PATENT DOCUMENTS

| | | |
|---|---|---|
| WO | WO95/27199 | 3/1995 |
| WO | WO99/60397 | 4/1999 |
| WO | WO01/09598 | 7/2000 |

OTHER PUBLICATIONS http://www.micronics.net/hfilter.htm, pp. 1-3, downloaded Jun.14, 2000.

http://www.micronics.net/mcytometry.htm, pp. 1-4, downloaded Jun. 14, 2000.

http://www.micronics.net/orcafluidics.htm, pp. 1-4, downloaded Jun. 14, 2000.

Altendorf et al., "Implementation Of Novel Optical Detection Methods For Clinically Important Blood Analytes Using Microfabricated Flow Structures (T-Sensors™)", MicroTAS 98, Banff, Canada, Apr. 1998.

Altendorf et al., "Differential Blood Cell Counts Obtained Using A Microchannel Based Flow Cytometer", Solid State Sensors & Actuators, vol. 1, 531, 1997.

Altendorf et al., "Microfabrication Technology For Research And Diagnostics, Silicon Microchannel Optical Flow Cytometry", SPIE Proceedings, Biomedical Optics 96, Jan. 1996.

Altendorf et al., "Results Obtained Using A Prototype Microfluidics-Based Hematology Analyzer", SPIE Biomedical Optics 97, 1997.

Cabuz, et al., "Mesoscopic Sampler Based on 3D Array of Electrostatically Activated Diaphragms", Transducers '99, The 10th International Conference on Solid-State Sensors and Actuators, Digest of Technical Papers, vol. 2, Jun. 7-10, 1999.

Darling et al., "Integration Of Microelectrodes With Etched Microchannels For In-Stream Electrochemical Analysis", MicroTAS 98, Banff, Canada, Apr. 1998.

Eyal et al., "Velocity-independent microfluidic flow cytometry," Electrophoresis, vol. 23, pp. 2653-2657, 2002.

Hatch et al., "Microfluidic Approaches To Immunoassays", SPIE conference on Micromachining and Microfabrication Symposium at Santa Clara, CA, Sep. 20-22, 1999.

Huang. et al., "Development Of A Flow Cytometry Based Miniature Chemical Fluid Analysis System Using Fluorescent Microbeads", SPIE Biomedical Optics, BIOS 97, conference proceedings, 1997.

Lehman et al., "High-Frequency Modulation Characteristics of Red VCSELs", Electronics Letters, Feb. 13, 1997, vol. 33(4), pp. 298-300. Copyright 1997 IEE.

Ohnstein et al., "Micromachined Silicon Microvalve", Proceedings of MEMS, 1990, IEEE Micro Electromechanical Systems, Napa Valley, California, Feb. 11-14, 1990, pp. 95-98.

Roulet et al., "Fabrication of Multilayer Systems Combining Microfluidic and Microoptical Elements for Fluorescence Detection," Journal of Microelectromechanical Systems, vol. 10, No. 4, pp. 482-491, Dec. 2001.

Shapiro, "Practical Flow Cytometry", third edition, 1995, p. 237.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen, et al., "Four-Parameter White Blood Cell Differential Counting Based on Light Scattering Measurements", Alan R. Liss, Inc., Cytometry 9:39-43, 1988.

Weigl et al., "Silicon-microfabricated diffusion-based optical chemical sensor," Sensors and Actuators, B 38-39, pp. 452-457, 1997.

Weigl et al., "Diffusion-Based Optical Chemical Detection In Silicon Flow Structures", Analytical Methods & Instrumentation, µTTAS 96 special edition, 1996.

Weigl et al., "Microfluidic Diffusion-Based Separation And Detection", Science, vol. 283, pp. 346-347, Jan 15, 1999.

Weigl et al., "Optical And Electrochemical Diffusion-Based Detection Of Analytes In Complex Samples Using Microfabricated Flow Structures (T-SensorSTM)", Micro- and nanofabn'cated electro-optical mechanical systems for biomedical and environmental applications II- SPIE vol. 3606, Jan. 25-26, 1999.

Weigl et al., "Rapid Sequential Chemical Analysis Using Multiple Fluorescent Reporter Beads", µTTAS 96 Conference Proceedings, 1996.

Weigl et al., "Simultaneous Self-Referencing Analyte Determination In Complex Sample Solutions Using Microfabricated Flow Structures (T-Sensors™)", Proceedings of MicroTAS 98, 81-4, Banff, Canada, 1998.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTm Technology", Medical Design Online, http://news.medicaldesignonline.com/featuresarticles/19990416-5922.html, Apr. 1999.

Weigl, et al., "Fluorescence and Absorbance Analyte Sensing In Whole Blood Based On Diffusion Separation In Silicon-Microfabricated Flow Structures," SPIE Proceedings, J. Lakowitz (ed.), Advances in Fluorescence Sensing Technology III, 1997, pp. 171-181.

Yager et al., "Design Of Microfluidic Sample Preconditioning Systems For Detection Of Biological Agents In Environmental Samples", SPIE Proceedings, 3515, 252-259, 1998.

Yager et al., "Applying Microfluidic Chemical Analytical Systems To Imperfect Samples", Micro Total Analysis Systems 98, Kluwer Academic Publishers, Dordrecht, 207-212, 1998.

* cited by examiner

CYTOMETER HAVING FLUID CORE STREAM POSITION CONTROL

BACKGROUND

The present invention relates generally to flow cytometers. More particularly, the present invention relates to flow cytometers that sense optical properties of microscopic particles or components in a flow stream.

This invention is related to U.S. patent application Ser. No. 10/225,325, by Bernard Fritz et al., filed Aug. 21, 2002, and entitled "Optical Alignment Detection System", which is incorporated herein by reference, and this invention is related to U.S. patent application Ser. No. 10/304,773, to Aravind Padmanabhan et al., filed Nov. 26, 2002, and entitled "Portable Scattering and Fluorescence Cytometer", which is incorporated herein by reference. This invention also is related to U.S. Pat. No. 6,549,275 B1, by Cabuz et al., issued Apr. 15, 2003, and entitled "Optical Detection System for Flow Cytometry"; U.S. Pat. No. 6,597,438 B1, by Cabuz et al., issued Jul. 22, 2003, and entitled "Portable Flow Cytometer"; U.S. Pat. No. 6,382,228 B1, by Cabuz et al., issued May 7, 2002, and entitled "Fluid Driving System for Flow Cytometry"; U.S. Pat. No. 6,700,130 B2, issued Mar. 2, 2004, by Fritz, and entitled "Optical Detection System for Flow Cytometry"; and U.S. Pat. No. 6,240,944 B1, by Ohnstein et al., issued Jun. 5, 2001, and entitled "Addressable Valve Arrays for Proportional Pressure or Flow Control"; all of which are incorporated herein by reference. The term "fluid" may be used here as a generic term that includes gases and liquids as species. For instance, air, gas, water and oil are fluids.

SUMMARY

The invention is a cytometer having a mechanism for aligning a fluid core stream in a channel.

DESCRIPTION

Figure 1:
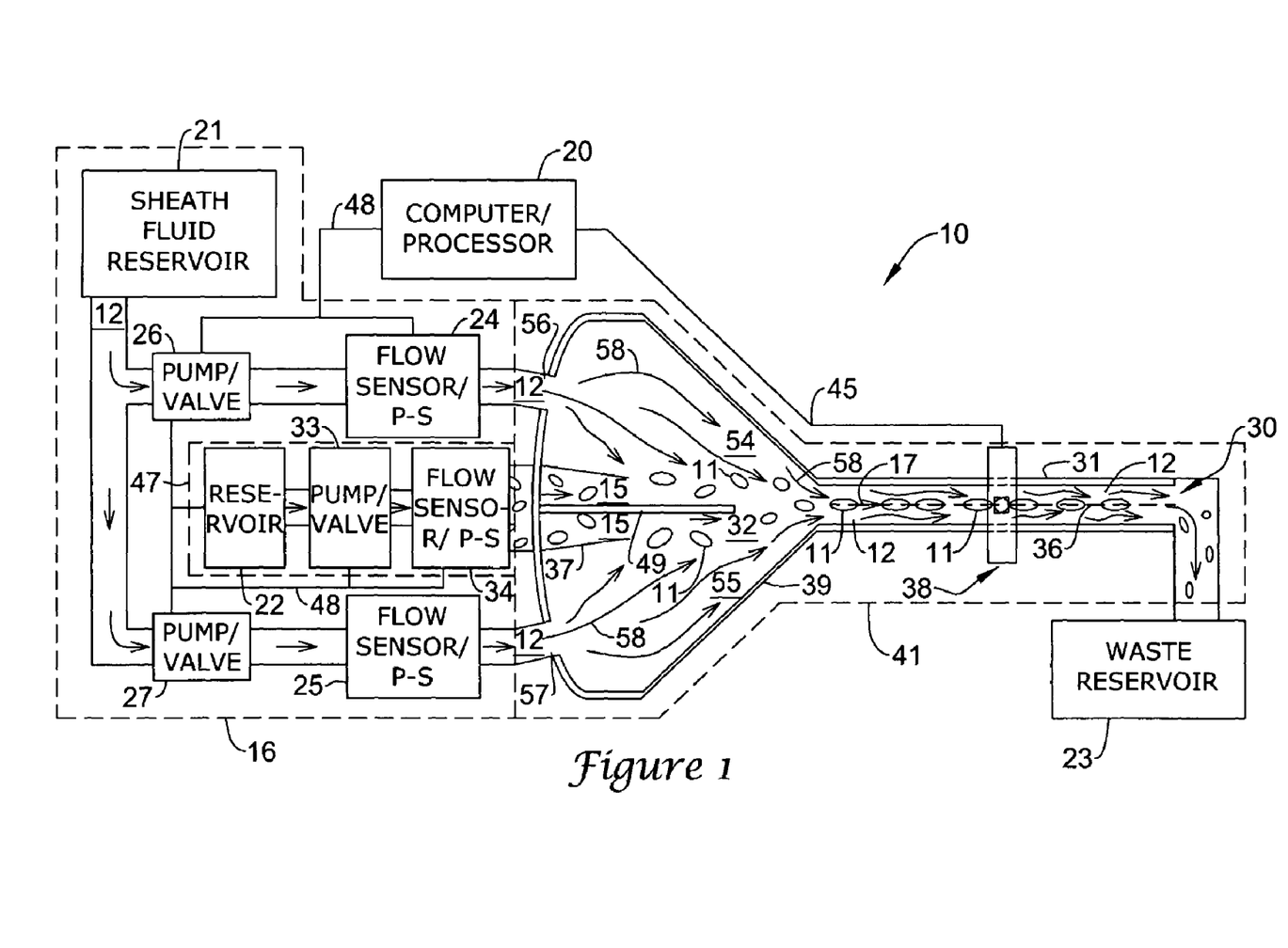
FIG. 1 is a diagram of a cytometer having two sheathing fluid chambers for controlling the position of the core stream.

Portions and components of cytometer 10 are not drawn to scale in FIG. 1. Portions of fluid circuits 16 and 47 and many of their components, along with computer/processor 20 and reservoir 23, in actuality, may be very much larger than the components of portion 41. Flow cytometry may be used to determine certain physical and chemical properties of microscopic biological particles or components 11 by sensing certain optical properties of those particles or components. To do so, for instance, the particles 11 may be arranged in single file using hydrodynamic focusing within a sheath fluid 12, as noted in FIG. 1. The particles 11 may then be individually interrogated by a light source and detector arrangement 38 in FIGS. 1 and 2. Each particle 11 may scatter a light beam 13 and produce a scatter 14 profile. The scatter 14 profile may be identified by measuring the light intensity at different scatter angles, such as with detector component 43. Component 43 may be an annular shaped detector. Certain physical and/or chemical properties of each particle 11 may then be determined from the scatter 14 profile. If no particle 11 is impinged by a light beam 13, then a detector 42 may output a signal indicating no particle present in the path of the light beam 13.

Figure 2:
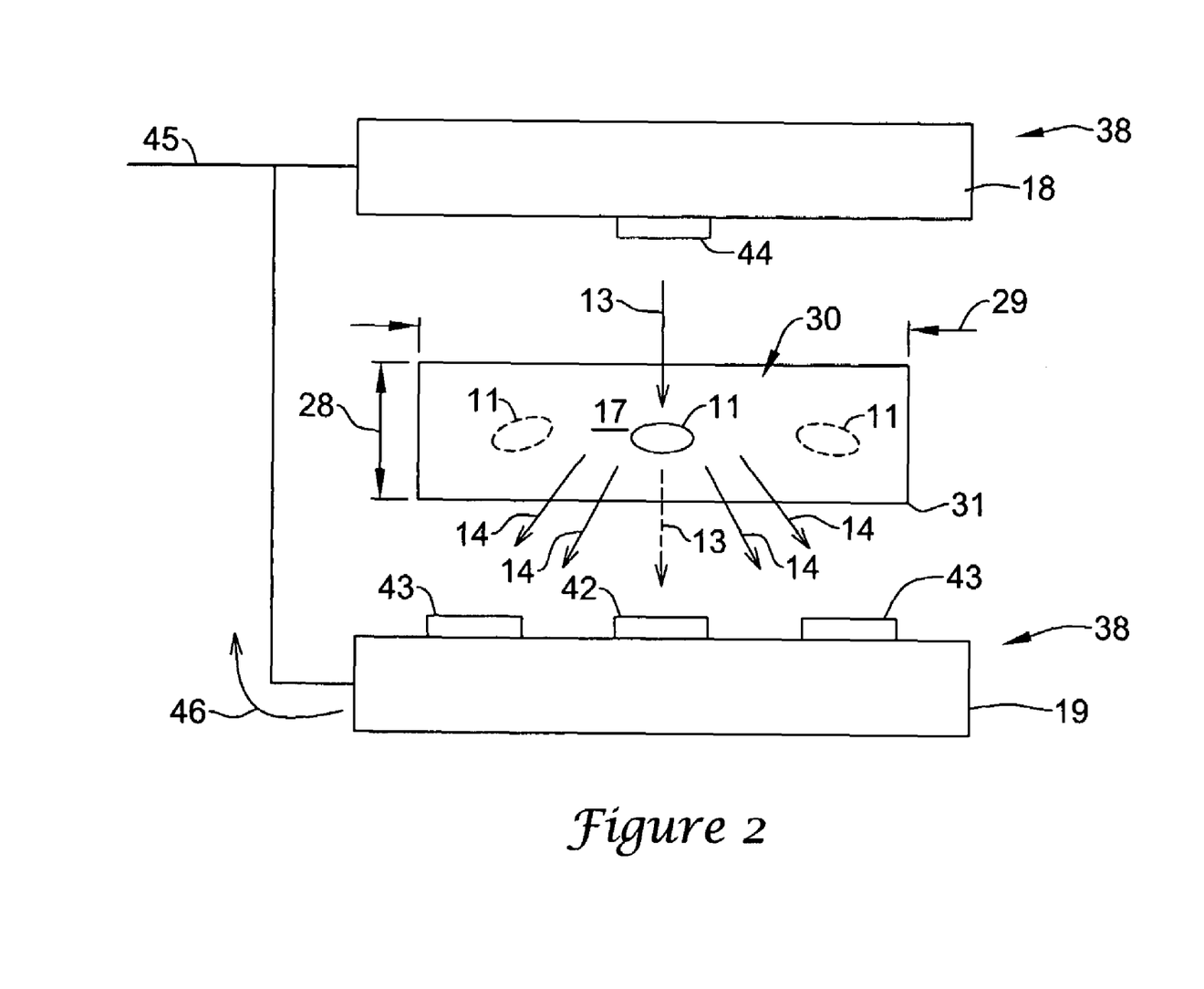
FIG. 2 is an end view of the light source and detector arrangement relative to the flow channel.

The controlled sample fluid 15 and supporting fluids 12 may be provided by fluidic circuits 16 and 47. A fluidic containment structure 39 may enclose hydrodynamic focusing that causes the desired particles 11 to fall into single file in a core stream 17 surrounded by a sheath fluid 12. One or more light sources 44 or light source arrangements 18 may provide light 13 through the core stream 17, and one or more light detectors 42, 43, or light detector arrangements 19 may detect the scatter 14 profiles and possible fluorescence of the particles 11 of a flow stream 30. Detector 43 may be an annular detector or an array of annular detectors. There may be a detector 42 positioned proximate to the center of the channel 31. An arrangement 38 may have one or more light sources 44 and/or one or more light detectors 42, 43. Arrangement 38 may include a single optical device or element arrangements 18 and 19 or an array of such items. A computer or processing block 20 may use output signals 46 via connection or line 45 from the light detector arrangement 19 to identify and/or count selected particles 11 in the core stream 17. FIG. 2 is a cross-section view of channel 31 at the light source-detector arrangement 38.

Flow sensors/pressure sensors (P-S) 24, 25, 34 may be provided in-line with each fluid prior to hydrodynamic focusing in region 32 of enclosure 39. Each flow sensor 24, 25, 34 may measure the velocity of the corresponding fluid. The flow sensors 24, 25, 34 may be thermal anemometer type flow sensors and/or microbridge type flow sensors. Pressure sensors 24, 25 and 34 may measure the pressures of the respective fluids 12 and 15.

The flow stream 30 may include a core stream 17 surrounded by a sheath fluid 12. Core stream 17 may be formed with hydrodynamic focusing with fluid 15 having particles 11 sheathed with a fluid 12, and may move along an axis 36 of channel 31. Particles 11 may be in suspension and in a focused flow of a single file. The fluid 15 with particles 11 may be injected from orifice 37 that may have a size between 50 and 200 microns. In FIG. 2, one dimension 28 of the channel 31 may be reduced so that the particles 11 are controlled in position in at least that dimension. The other dimension 29 may be several times larger to reduce light reflection problems internal to the channel 31. An illustrative example of dimensions 28 and 29 may be 50 microns and 200 microns, respectively. Typical particles 11 may vary from 2 microns to 20 microns. Maintaining an appropriate position of the particles 11 in the midst of the larger dimension 29 may be achieved with control of the sheathing fluid 12 via parameters such as pressure and or flow of the latter.

The velocity of the sheath fluid 12 may be different than that of the core stream 17 for a laminar flow. However, the velocity of the sheath fluid 12 and core stream 17 may remain sufficiently low to maintain laminar flow in the flow channel 31. Fluid 12 may enter through input port 56 into region 54 from reservoir 21 via pump/valve 26 and flow sensor/pressure sensor 24. Fluid 12 may enter through input port 57 into region 55 from reservoir 21 via pump/valve 27 and flow sensor/pressure sensor 25. The fluid 15 with particles 11 may have a low volume flow rate whereas the sheath fluid volume flow rate may be larger and set by the sheath fluid 12 pressures in regions 54 and 55 of containment 39. A barrier 49 may be a dividing wall between the channels or regions 54 and 55. A difference in pressure between fluid 15 and fluid 12 may be used to control the fluid 15 volume flow rate. The achievement of hydrodynamic focusing may depend on a laminar flow in which fluid 15 with its particles flows in central core stream that does not mix with the sheath fluid 12. Whether a flow is laminar may be determined from a Reynolds number ($R_e$). $R_e = d\rho\bar{v}/\eta$, where d is a tube diameter or a diameter equivalent of channel 31 dimensions, $\rho$ is fluid density, $\bar{v}$ is the mean velocity of the fluid and $\eta$ is the viscosity of the fluid. When $R_e$ is less than 2300, the flow is laminar. When $R_e$ is greater than 2300, then the flow may be turbulent.

As particles 11 are hydrodynamically focused, they may be subject to shear stresses which may cause the particles to have their longer dimension (if any) oriented along the axis of their flow direction. Such shear forces may cause some particles to be somewhat elongated in the direction of flow.

In flow cytometer 10 using optical scattering, the particles 11 may be centered on the focused optical light beam 13 in order to achieve high signal-to-noise and accuracy in measurements. Adjustment of the location of the fluid core stream 17 containing the particles 11 such as cells may be accomplished by varying the flow parameters, (e.g., velocity, pressure and the like) of the surrounding sheathing fluid 12 in independent regions 54 and 55 during the injection process from nozzle or orifice 37 at the hydrodynamic focusing region 32. A control loop may be established between channel 31 having an optical light emitting and detection arrangement 38 (i.e., a light source 44 with a focused beam 13 and light detectors 42 and 43) and the control of the flow parameters (i.e., pressure and/or volume via pumps/valves 26 and 27 connected to computer/processor 20) in the sheathing fluid 12 portions in segments or regions 54 and 55 to move the core 17 with particles 11 to or from the center axis 36 where the focused light beam 13 is located so as to maximize or minimize (e.g., null) the optical light signals 13 and/or 14, which in turn may send corresponding electrical signals 46 to computer/processor 20 along an electrical conductor 45. Flow/pressure sensors 24 and 25 may monitor the differential flow and pressure of fluid 12 going into regions 54 and 55. These components may be connected to the computer/processor 20. As needed in maintaining control of the hydrodynamic focusing of core stream 17, the pump/valve 33 and flow/pressure sensor may be connected to computer/processor 20.

A flow cytometer measurement channel 31 may consist of a core region 17 of laminar flow containing the isolated particles 11 to be measured surrounded by a region of sheathing fluid 12. Both sheathing and particle 11 fluid regions may be injected into the measurement channel 31 by way of a hydrodynamic focusing mechanism. For a cytometer 10 which uses optical scattering as a measurement mechanism, it may be important to place the particles 11 substantially in the focused optical beam formed by the light source 18. This factor may be accomplished by adjusting the focused beam 13 to coincide with the particular location of the core 17 channel 31, and this may require the use of either multiple optical sources or a mechanical mechanism to translate or steer the optical beam 13. The same task may be accomplished by using a simple, fixed optical source 18/detector 19 module arrangement 38, adjusting the flow configuration to move the core stream 17, containing the fluid 15 with particles 11, sideways in channel 31 to the location of focused optical light beam 13. This may be done by dividing the sheathing fluid 12 into a number of independent channels, segments or regions 54 and 55, as shown in FIG. 1, at the injection nozzle or orifice 37 region of the hydrodynamic focusing device. The sheathing fluid 12 may surround the central core stream 17 and generally keep the core stream 17 away from the walls of the measurement channel 31 and maintain the core stream in a laminar flow. The location of core stream 17 may be determined by the specific flow parameters (e.g., pressure and/or flow) of the sheathing fluid 12 segments in regions 54 and 55, respectively, and thus by varying these parameters, the core stream's location may be made to coincide with the focused optical light beam 13. These parameters may be controlled via pump/valve 26 and pump/valve 27 by the computer/processor 20. This may be implemented with a feedback control loop between the electrical signal 46 produced by the source-particle-detector assembly 38 and the sheathing fluid 12 flow circuit 16. Fluid 15 may be controlled by fluid circuit 47. Component pumps/valves 26, 27, 33, and flow/pressure sensors 24, 25, 34, may be electrically connected to computer/processor 20 via conductors 48. Also, there may be fluid level indicators in reservoirs 21 and 22 connected via conductors 48 to computer/processor 20.

Figure 3:
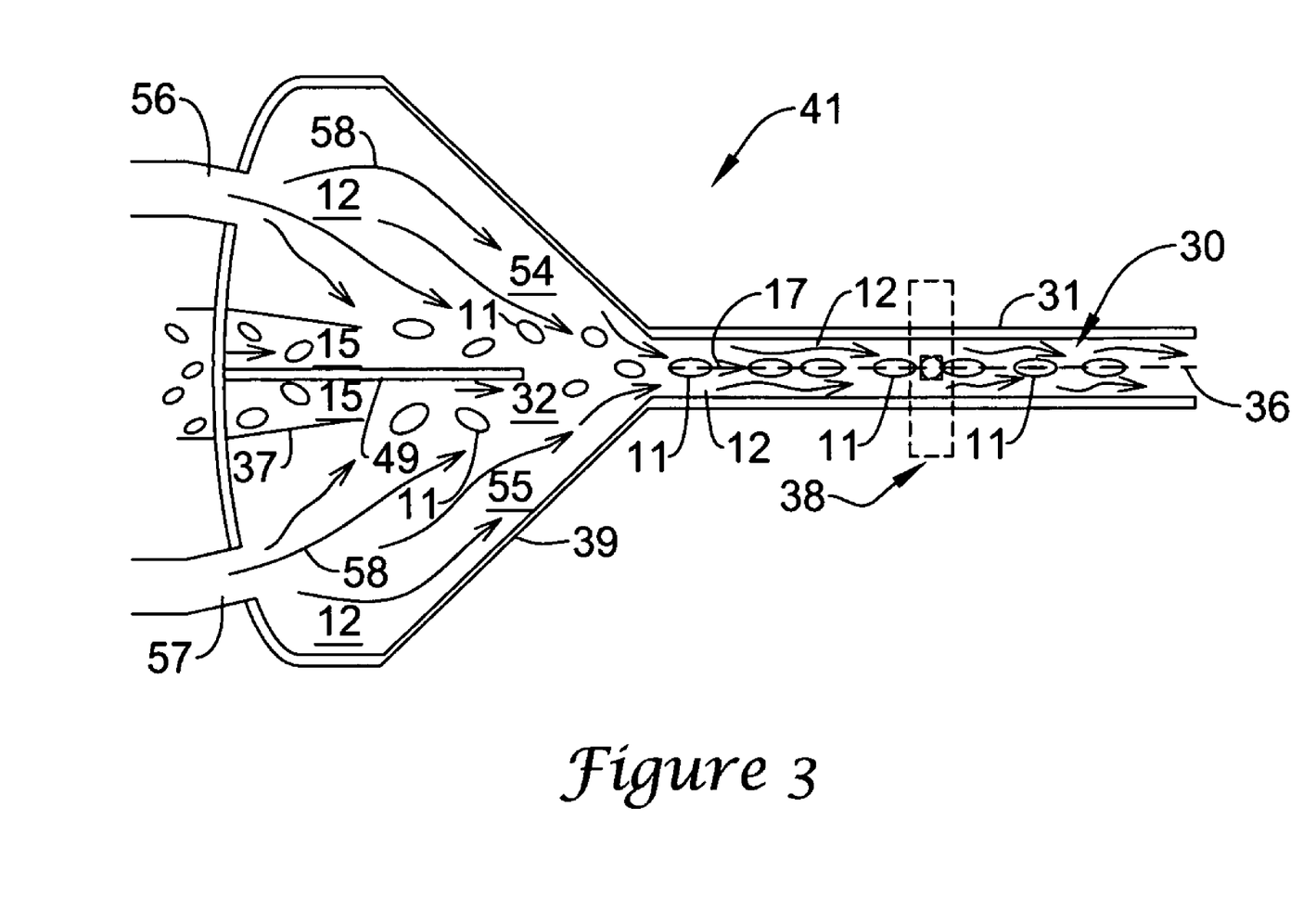
FIGS. 3-5 show three different alignments of the core stream relative to the central axis in the flow channel.
Figure 4:
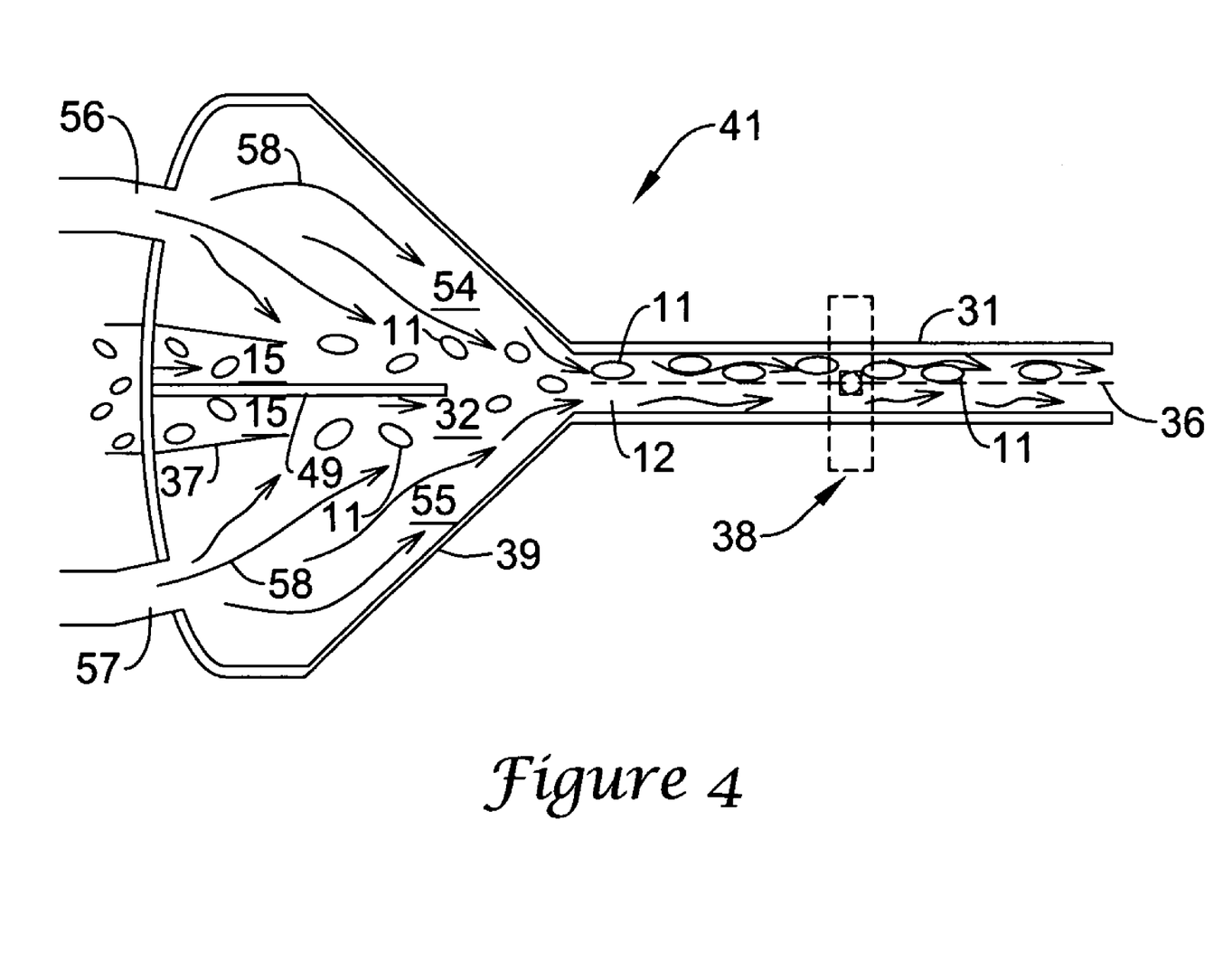
Figure 5:
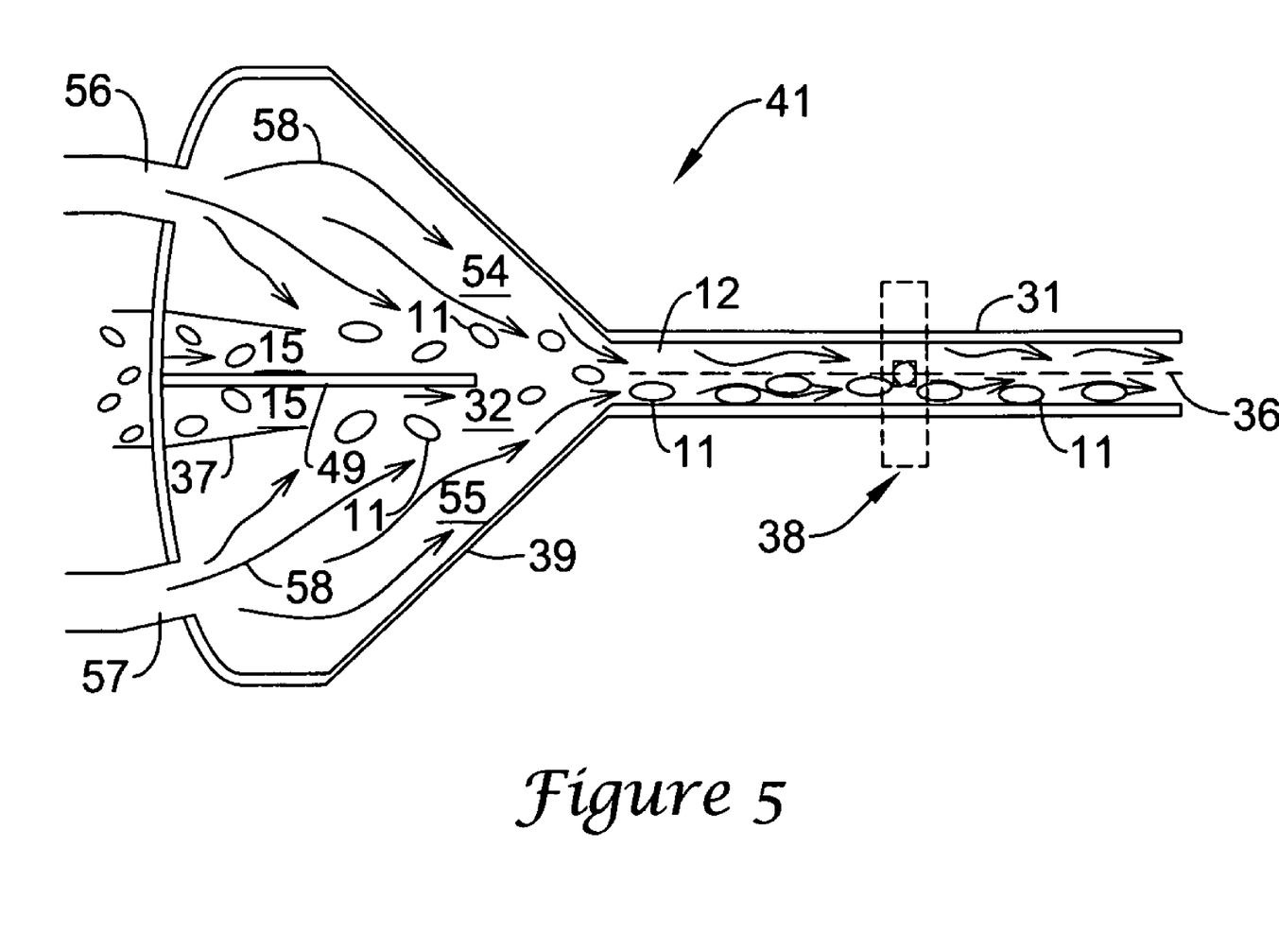

FIGS. 3-5 show the various alignments of flow stream 17 with axis 36 of channel 31. FIG. 3 shows the flow stream 17 and respective particles 11 aligned with axis 36. FIG. 4 shows the flow stream 17 and respective particles 11 to be off relative to axis 36 in one direction, and FIG. 5 shows the flow stream 17 and respective particles 11 to be off relative to axis 36 in the other direction. Looking down the channel 31 towards the discharge end, the dashed sketch of particle 11 to the left of axis 36 represents the misalignment in FIG. 4, and the dashed sketch of particle 11 to the right of axis 36 represents the misalignment in FIG. 5.

Figure 6:
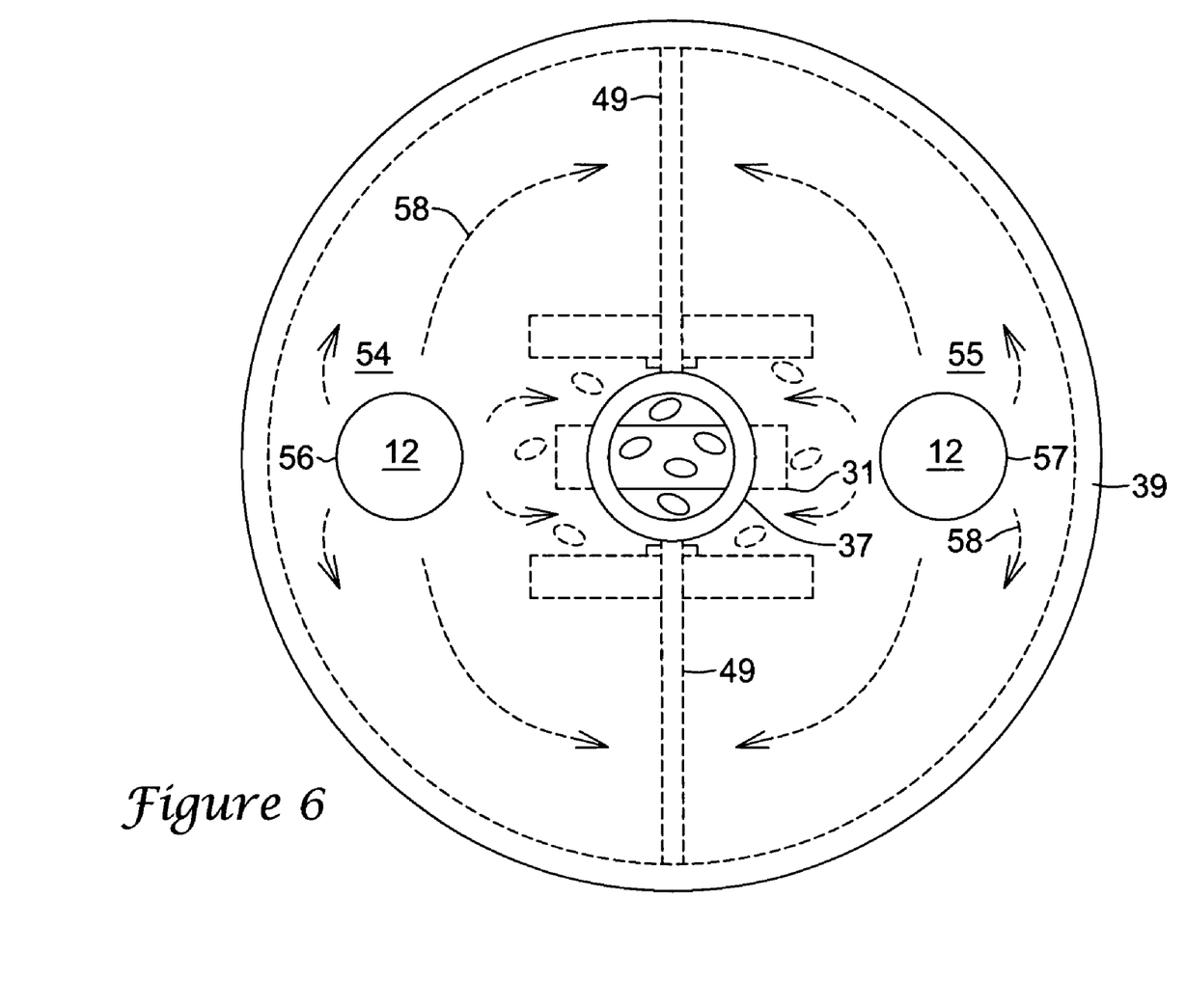
FIGS. 6-9 show and end view of a containment having two, four, six and eight sheathing fluid channels, chambers, segments or regions, respectively.
Figure 7:
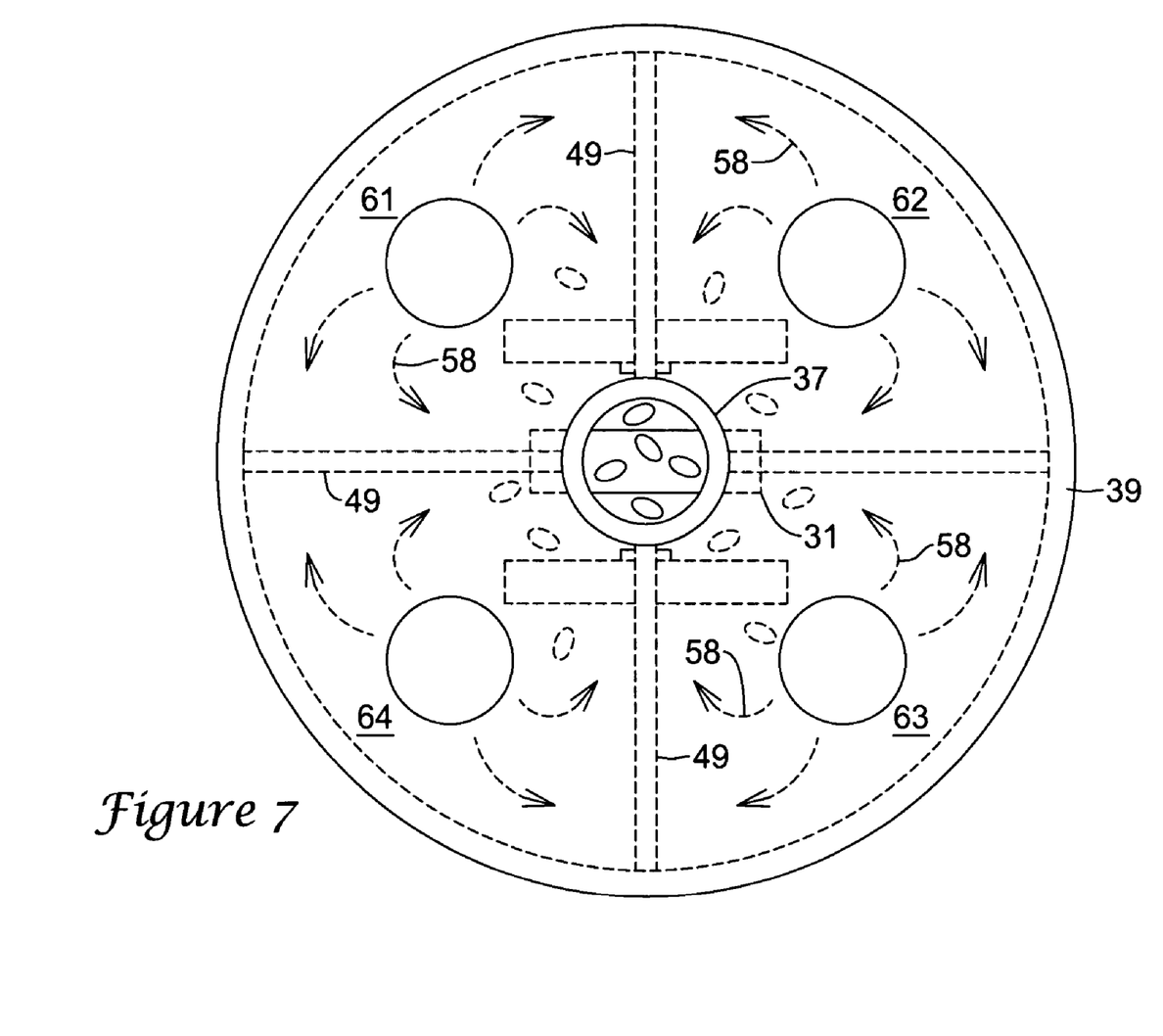
Figure 8:
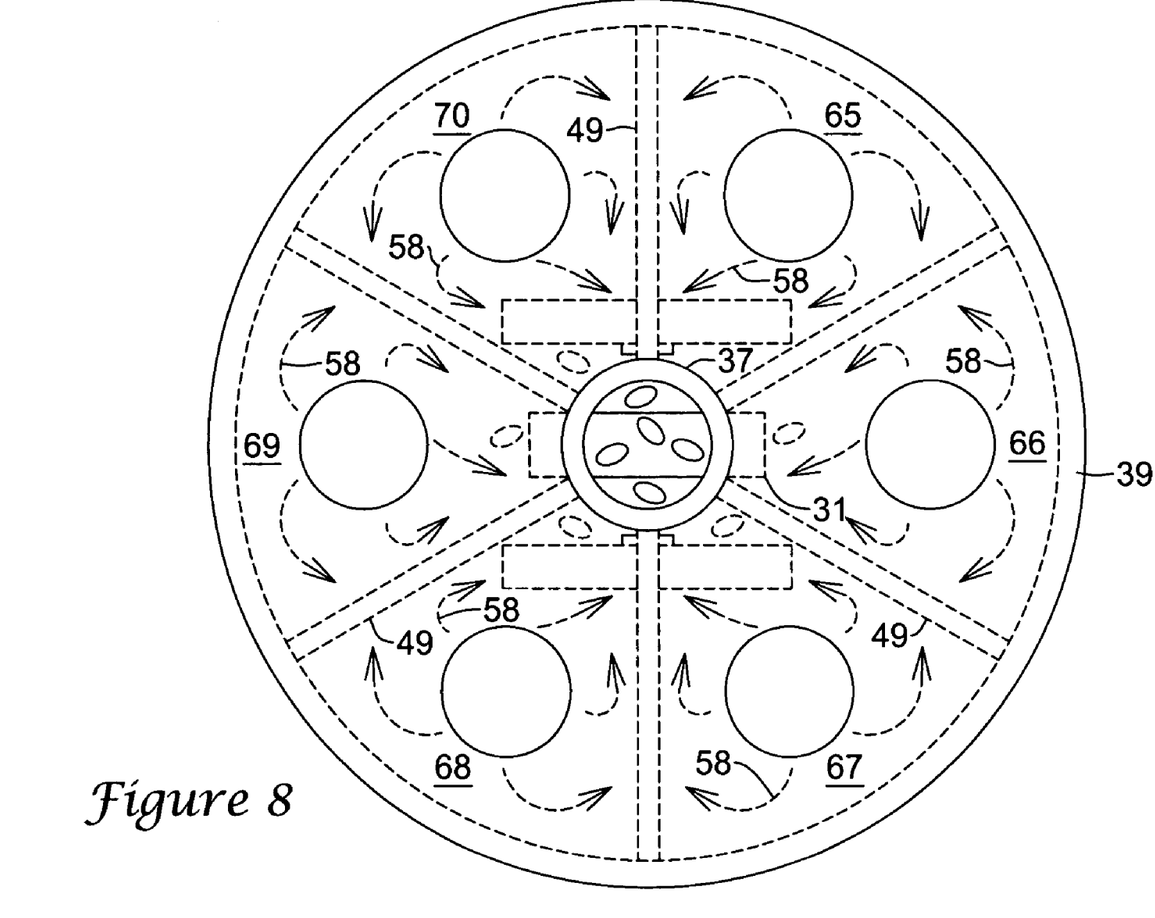
Figure 9:
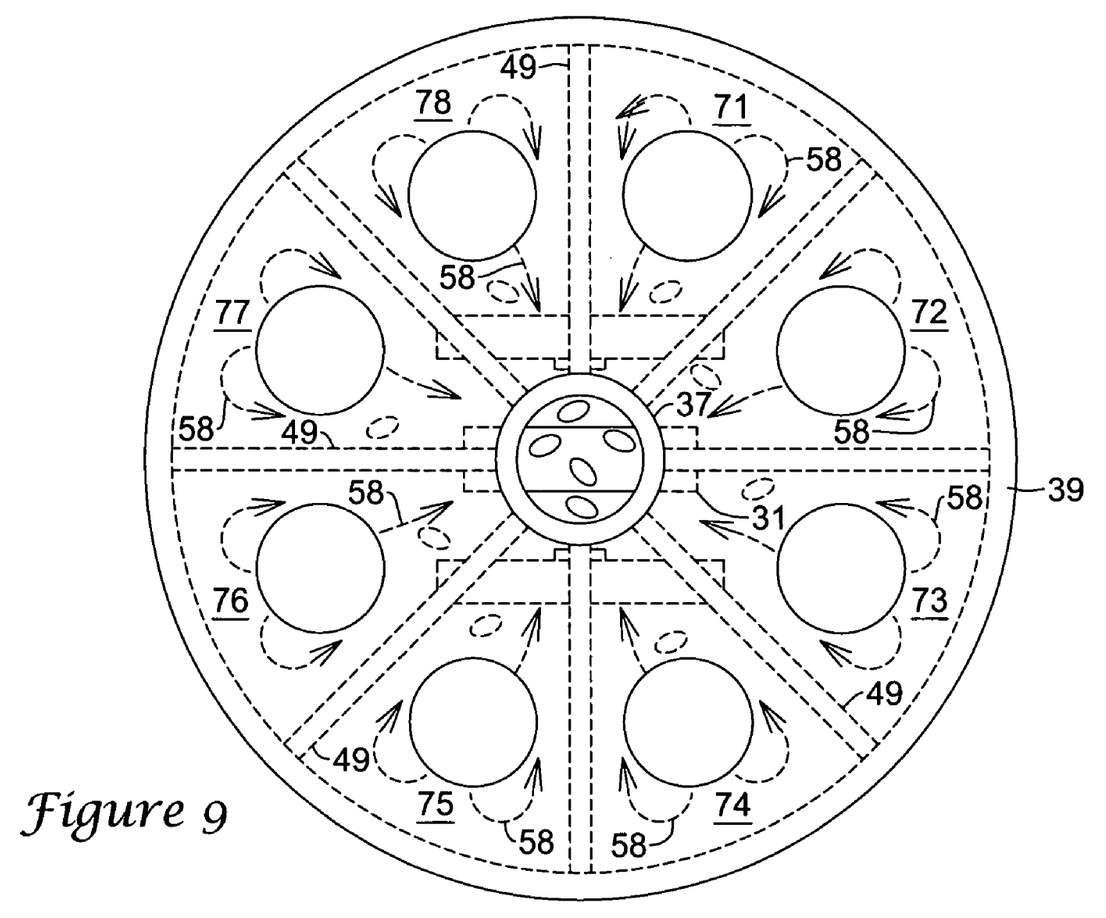

FIG. 6 shows an end view of containment 39 having two sheathing fluid 12 regions or channels 54 and 56. Divider or barrier 49 may establish these regions. The controlling sheathing fluid may have more than two regions in containment 39, along with the corresponding additional pumps/valves, flow sensors/pressure sensors, as needed, and respective connections to computer/processor 20 to control the core stream 17 in channel 31. For instance, FIG. 7 shows containment 39 having four regions 61, 62, 63 and 64 delineated by barriers 49. FIG. 8 shows the containment with six regions 65, 66, 67, 68, 69 and 70, and FIG. 9 shows containment 39 with eight regions 71, 72, 73, 74, 75, 76, 77 and 78.

Figure 10:
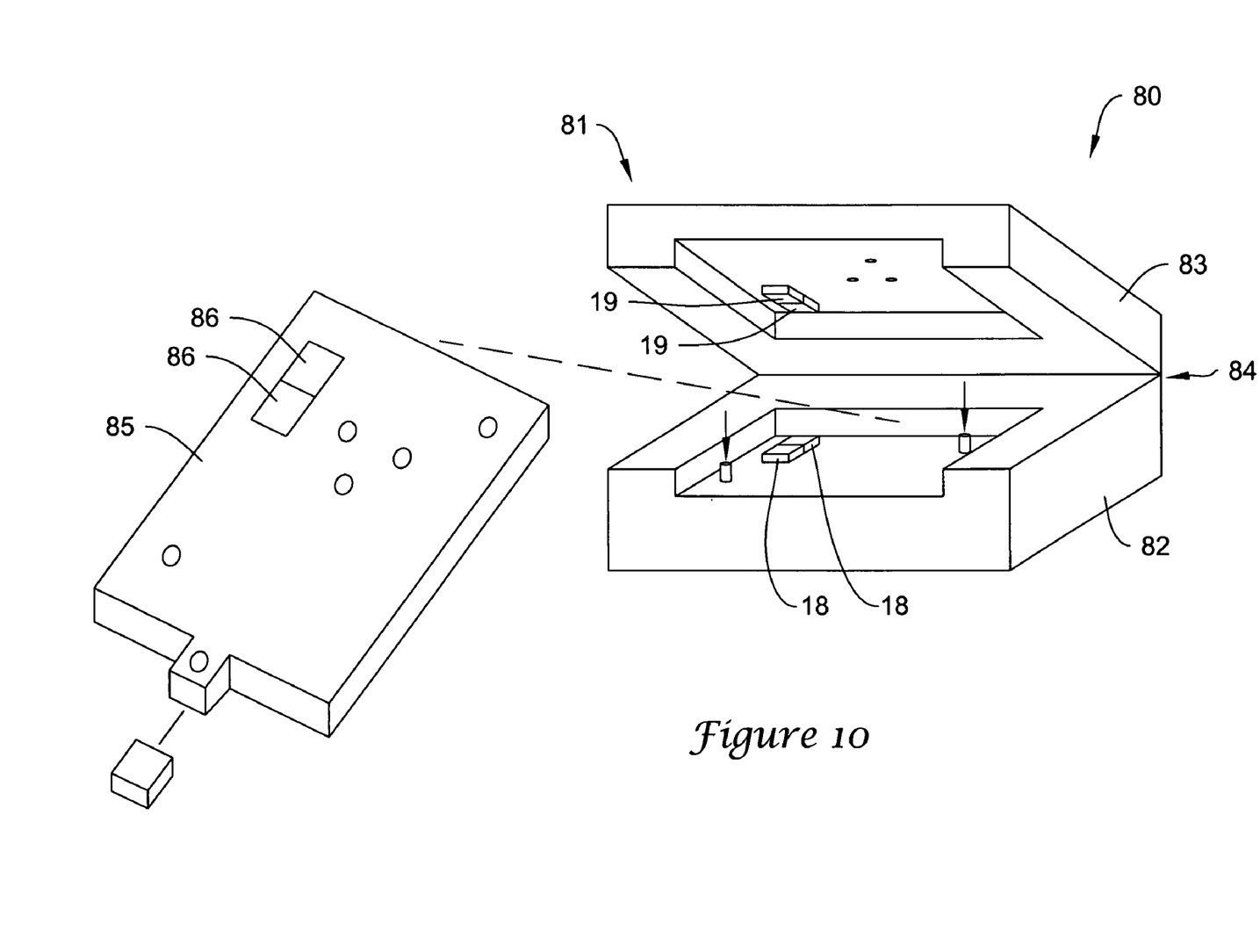
FIG. 10 reveals an illustrative example of a miniaturized housing for the present cytometer.

There may be a miniaturized portable version 80 of cytometer 10 provided in a housing 81 sufficiently small to be appropriately and comfortably wearable on a person. As one illustrative example in FIG. 10, the housing 81 may be sized similar to a wrist watch. The wearable housing 81 may include, for example, a base 82, a cover 83, and a fastener 84 that secures the base 82 to the cover 83. The fluid drivers or pumps 26, 27, 33, including regulating valves, respectively, of fluid circuits 16 and 44, may be incorporated into the cover 83, while the fluid reservoirs 21, 22, 23, and flow sensors/pressure sensors (P-S) of fluidic circuit 16 may be incorporated into a removable cartridge 85 that is inserted into the housing 81. Core stream 17 may be illuminated through channel windows 86 of the flow stream 30. The fluidic circuits 47 and 16, as an illustrative example, may dilute a blood sample, perform red cell lysing, and perform hydrodynamic focusing for core stream 17 formation and control. The light source(s) 18 may be situated in either the base 82 or the cover 83, and aligned with the flow stream 17 of the removable cartridge 85. The light detector(s) 19 may be provided generally opposite of the light source(s) 19. The processor 20 and batteries may be provided in either the base 82 or the cover 83 of the housing 81. The light source(s) 18, light detector(s) 19, and associated control and processing electronics 20 may perform differentiation and counting of the particles 11, and feedback for control of the core stream 17 in channel 31, based on light beam 13 and light scattering 14 signals.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A cytometer system comprising:
    a flow channel having an axis;
    a hydrodynamic focusing channel connected to the flow channel;
    an injection channel connected to the hydrodynamic focusing channel for injecting a sample into the hydrodynamic focusing channel;
    a first sheath fluid channel connected to the hydrodynamic focusing channel for delivering a first sheath fluid to a first part of the hydrodynamic focusing channel at a first flow rate;
    a second sheath fluid channel connected to the hydrodynamic focusing channel for delivering a second sheath fluid to a second part of the hydrodynamic focusing channel at a second flow rate;
    a light source proximate to the flow channel;
    a light detector proximate to the flow channel for detecting a core stream in the flow channel, wherein the core stream in the flow channel includes at least part of the sample injected by the injection channel; and
    a feedback control loop coupled to the detector for controlling a relative measure of the first and second flow rates in the first and the second sheath fluid channels, the feedback control loop adjusting a relative measure of the first flow rate and the second flow rate to move the position of the core stream in the flow channel to a desired position relative to the light detector.

2. The system of claim 1, further comprising:
    a first flow rate control mechanism connected to the first sheath fluid channel; and
    a second flow rate control mechanism connected to the second sheath fluid channel.

3. The system of claim 2, wherein the feedback control loop includes a processor connected to the detector, the first flow rate control mechanism and the second flow rate control mechanism.

4. The system of claim 3, wherein:
    the detector provides a signal to the processor indicating a position of the core stream relative to the axis of the flow channel;
    the first and second flow rate control mechanisms affect an alignment of the core stream relative to the axis of the flow channel by changing the first flow rate and/or the second flow rate; and
    the processor provides signals to the first and second flow rate control mechanisms in response to a signal from the detector to effect the alignment of the core stream relative to the axis of the flow channel by adjusting at least one of the first and second flow rates.

5. The system of claim 4, wherein the signals to the first and second flow rate control mechanisms in response to the signal from the detector aligns the core stream relative to the axis of the flow channel by adjusting the position of the core stream in at least two dimensions.

6. The system of claim 1, wherein the first and second sheath fluid channels are separated by at least one barrier extending inward toward the injection channel.

7. A method aligning a core stream in a flow channel of a cytometer, comprising:
    providing a sample fluid;
    providing a first sheath fluid proximate to the sample fluid;
    providing a second sheath fluid proximate to the sample fluid; and
    hydrodynamically focusing the sample fluid into a core stream with the first and second sheath fluids into a flow channel;
    measuring the flow rate of the first sheath fluid;
    measuring the flow rate of the second sheath fluid;
    adjusting the relative flow rate of the first and second sheath fluids to move the position of the core stream in a desired direction.

8. The method of claim 7, further comprising providing a third sheath fluid proximate to the sample fluid, and hydrodynamically focusing the sample fluid into the core stream with the first, second and third sheath fluids into the flow channel, and further including adjusting the relative flow rate of the first, second and third sheath fluids to affect a desired alignment of the core stream relative to the flow channel.

9. The method of claim 8, further comprising differentially adjusting flows of the first, second, and third sheath fluids to align the core stream relative to an axis of the flow channel.

10. The method of claim 9, further comprising determining the alignment of the core stream with a light source and detector proximate to the flow channel.

11. The method of claim 10, wherein:
    the core stream comprises particles that scatter light from the light source;
    the detector detects the light scattered by the particles; and
    a magnitude of scattered light by the particles is indicative of a position of the core stream relative to the axis of the flow channel.

12. A means for aligning a cytometer, comprising:
    means for providing a sample fluid;
    means for providing a plurality of sheathing fluids;
    means for hydrodynamically focusing the sample fluid into a core stream with the plurality of sheathing fluids; and
    means for individually sensing and controlling the flows of the plurality the sheathing fluids to effect an alignment of the core stream relative to an axis of a flow channel.

13. The means of claim 12, further comprising means for detecting the alignment of the core steam relative to the axis of the flow channel.

14. The means of claim 13, further comprising means for providing information from the means for detecting to the means for individually sensing and controlling the flows of the plurality of the sheathing fluids to maintain an alignment of the core stream.

* * * * *